United States Patent [19]

Schröter et al.

[11] 4,304,912
[45] Dec. 8, 1981

[54] PIPERIDINE DERIVATIVES

[75] Inventors: Herbert Schröter, Füllinsdorf; Kurt Eichenberger, Therwil; Hans Kühnis, Basel; Christian Egli, Magden; Oswald Schier, Oberwil; Franz Ostermayer, Riehen, all of Switzerland

[73] Assignee: Ciba-Geigy Corporation, Ardsley, N.Y.

[21] Appl. No.: 102,462

[22] Filed: Dec. 10, 1979

Related U.S. Application Data

[63] Continuation of Ser. No. 926,356, Jul. 20, 1978, abandoned.

[51] Int. Cl.³ .................. C07D 209/12; C07D 217/22; C07D 241/18; A01K 31/445
[52] U.S. Cl. .................... 544/405; 546/141; 546/201; 424/250; 424/256; 424/258; 424/262
[58] Field of Search .................... 544/405; 546/141

[56] References Cited

U.S. PATENT DOCUMENTS 4,144,344  3/1979  Eichenberger et al. ............ 546/141
4,193,995  3/1980  Wasson et al. ..................... 544/405

FOREIGN PATENT DOCUMENTS 850556  2/1977  Belgium .
2533567  2/1976  Fed. Rep. of Germany ...... 544/405

*Primary Examiner*—Anton H. Sutto

*Attorney, Agent, or Firm*—Prabodh I. Almaula

[57] ABSTRACT

Piperidines of the formula

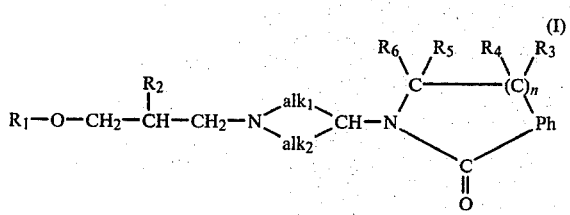

in which $R_1$ is a substituted or unsubstituted heteroaryl radical, $alk_1$ and $alk_2$ independently of one another are lower alkylene radicals, each of which separates by 2 carbon atoms the nitrogen atom bonded thereto from the methane group bonded thereto, $R_2$ is a free or acylated hydroxyl group, Ph is a substituted or unsubstituted o-phenylene radical, n is 0 or 1, $R_3$ is a hydrogen atom, a lower alkyl radical or a hydroxyl group and $R_5$ is a lower alkyl radical or a hydrogen atom, or $R_3$ and $R_5$ together are a second bond and $R_4$ and $R_6$ are each a hydrogen atom, or $R_4$ together with $R_3$ is an oxo group, $R_5$ is a lower alkyl radical or a hydrogen atom and $R_6$ is a hydrogen atom, or $R_6$ together with $R_5$ is an oxo group, $R_3$ is a hydrogen atom, a lower alkyl radical or a hydroxyl group and $R_4$ is a hydrogen atom, or salts thereof are antihypertensive and antiarrhythmic agents.

5 Claims, No Drawings

PIPERIDINE DERIVATIVES

This is a continuation of application Ser. No. 926,356 filed on July 20, 1978, now abandoned.

The invention relates to novel piperidine derivatives of the formula I

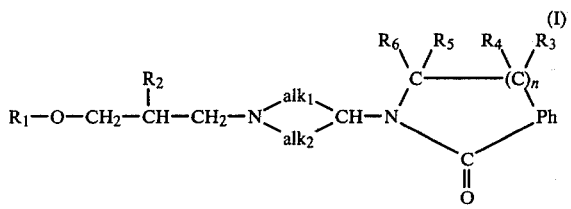

in which $R_1$ is a substituted or unsubstituted heteroaryl radical, $alk_1$ and $alk_2$ independently of one another are lower alkylene radicals, each of which separates by 2 carbon atoms the nitrogen atom bonded thereto from the methine group bonded thereto, $R_2$ is a free or acylated hydroxyl group, Ph is a substituted or unsubstituted o-phenylene radical, n is 0 or 1, $R_3$ is a hydrogen atom, a lower alkyl radical or a hydroxyl group and $R_5$ is a lower alkyl radical or a hydrogen atom, or $R_3$ and $R_5$ together are a second bond and $R_4$ and $R_6$ are each a hydrogen atom, or $R_4$ together with $R_3$ is an oxo group, $R_5$ is a lower alkyl radical or a hydrogen atom and $R_6$ is a hydrogen atom, or $R_6$ together with $R_5$ is an oxo group, $R_3$ is a hydrogen atom, a lower alkyl radical or a hydroxyl group and $R_4$ is a hydrogen atom, and salts thereof, as well as processes for the preparation of these compounds and pharmaceutical preparations containing these compounds.

When n is 1, the invention relates to compounds of the formula

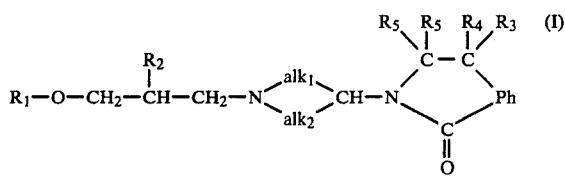

and when n is 0, the invention relates to compounds of the formula

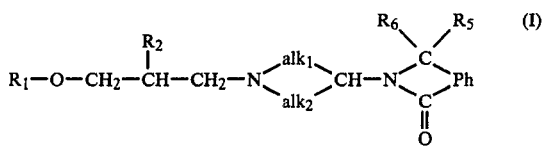

in which formulae $R_1$, $R_2$, $R_3$, $R_4$, $R_5$, $R_6$, Ph, $alk_1$ and $alk_2$ are as defined above.

Unless otherwise stated, lower radicals are those radicals which contain not more than 7 carbon atoms and preferably not more than 4 carbon atoms.

A heteroaryl radical $R_1$ is a substituted or unsubstituted heterocyclic, preferably monocyclic, or also bicyclic, heteroaryl radical, in particular a substituted, for example monosubstituted, disubstituted or polysubstituted, or unsubstituted, preferably monocyclic, azaaryl radical having 5 to 6 ring members and 1 to 2 ring nitrogen atoms, such as substituted or unsubstituted pyridyl, for example 2-, 3- or 4-pyridyl, imidazolyl, for example 2-imidazolyl, pyrimidinyl, for example 2- or 4-pyrimidinyl, pyridazinyl, for example 2-pyridazinyl, or pyrazinyl, for example 2-pyrazinyl, and also a substituted or unsubstituted bicyclic azaaryl radical, especially a benzoazaaryl radical, having 5 to 6 ring members and 1 to 2 ring nitrogen atoms in the araaryl radical, such as substituted or unsubstituted indolyl, for example 4-indolyl, quinolinyl, for example 4-quinolinyl, or isoquinolinyl, for example 1-isoquinolinyl. Substituents of a heteroaryl radical are, inter alia, substituted or unsubstituted aliphatic hydrocarbon radicals, free, etherified or esterified hydroxyl or mercapto, acyl, nitro or substituted or unsubstituted amino.

Lower alkylene radicals $alk_1$ and $alk_2$ are, for example, 2,3-butylene radicals, 1,2-butylene radicals, 1,1-dimethyl-1,2-ethylene radicals or preferably 1,2-propylene radicals or especially 1,2-ethylene radicals.

The o-phenylene radical Ph can carry one, two or more substituents; however, it preferably does not contain more than two substituents. Substituents of the o-phenylene radical are, in particular: lower alkyl radicals, lower alkoxy groups, halogen atoms, trifluoromethyl groups, hydroxyl groups and also, less preferentially, acylamino groups, nitro groups and amino groups.

A free or acylated hydroxyl group $R_2$ is, for example, a lower alkanoyloxy group, for example an acetoxy, propionyloxy or butyryloxy group or preferably the pivaloyloxy group, or in particular a free hydroxyl group.

Substituted or unsubstituted aliphatic hydrocarbon radicals as substituents of a heteroaryl radical $R_1$ are corresponding lower alkyl, and also lower alkenyl or lower alkynyl, substituents of lower alkyl being, in particular, free, etherified or esterified hydroxyl or mercapto, acyl or substituted or unsubstituted amino.

Lower alkyl radicals are, for example, methyl, ethyl, n-propyl or isopropyl radicals, or straight-chain or branched butyl, pentyl or hexyl radicals, which can be bonded in any position.

Lower alkenyl radicals are especially allyl or methallyl radicals and a lower alkynyl radical is in particular the propargyl radical.

Etherified hydroxyl is especially lower alkoxy or phenyl-lower alkoxy, and also lower alkenyloxy or lower alkynyloxy, as well as hydroxy-lower alkoxy, lower alkoxy-lower alkoxy, lower alkylthio-lower alkoxy or lower alkanoyl-lower alkoxy, whilst esterified hydroxyl is in particular halogen and also lower alkanoyloxy.

Etherified mercapto is in particular lower alkylthio, whilst esterified mercapto is, for example, lower alkanoylthio.

Acyl is preferably the corresponding radical of an organic carboxylic acid and is, for example, aroyl or lower alkanoyl. Acyl is also the corresponding radical of a carbonic acid half-derivative, such as lower alkoxycarbonyl or substituted or unsubstituted carbamoyl. In the broadest sense of the definition, cyano is also an acyl radical. Preferred acyl radicals are in particular benzoyl or acetyl.

Substituted or unsubstituted amino is acylamino, especially lower alkanoylamino or lower alkoxycarbonylamino, and also substituted or unsubstituted ureido. Substituted amino is also lower alkylamino or di-lower alkylamino, as well as lower alkyleneamino, lower oxaalkyleneamino or lower azaalkyleneamino, the azanitrogen in the latter preferably being substituted, for example by lower alkyl.

Lower alkoxy is, for example, methoxy, ethoxy, npropoxy, isopropoxy, n-butoxy or isobutoxy.

Phenyl-lower alkoxy is, for example, benzyloxy or 1- or 2-phenylethoxy.

Hydroxy-lower alkoxy is, for example, 2-hydroxyethoxy and also 2- or 3-hydroxypropoxy.

Lower alkoxy-lower alkoxy is, inter alia, lower alkoxymethoxy or 1- and especially 2-lower alkoxy-ethoxy, for example methoxy-methoxy, 2-methoxy-ethoxy or 2-ethoxy-ethoxy.

Lower alkylthio-lower alkoxy is, in particular, lower alkylthiomethoxy or 1- and in particular 2-lower alkylthio-ethoxy, for example 2-methylthio-ethoxy or 2-ethylthio-ethoxy.

Lower alkanoyl-lower alkoxy is, in particular, acetonyloxy.

Lower alkenyloxy is, for example, allyloxy, 2- or 3-methallyloxy or 3,3-dimethylallyloxy.

Lower alkynyloxy is, in particular, propargyloxy.

Halogen is preferably halogen with an atomic number of not more than 35, i.e. fluorine, chlorine or bromine.

Lower alkanoyloxy is, for example, acetoxy, propionyloxy or pivaloyloxy.

Lower alkylthio is, for example, methylthio, ethylthio, n-propylthio or isopropylthio.

Lower alkanoylthio is, inter alia, acetylthio or propionylthio.

Lower alkanoyl is, for example, acetyl, propionyl or butyryl.

Lower alkoxycarbonyl is, for example, methoxycarbonyl or ethoxycarbonyl.

Substituted or unsubstituted carbamoyl is, for example, carbamoyl or N-lower alkyl- or N,N-di-lower alkylcarbamoyl, such as N-methyl-carbamoyl, N,N-dimethylcarbamoyl, N-ethylcarbamoyl or N,N-diethylcarbamoyl.

Lower alkanoylamino is, for example acetylamino or propionylamino.

Lower alkoxycarbonylamino is, for example, methoxycarbonylamino or ethoxycarbonylamino.

Substituted or unsubstituted ureido is, for example, ureido or 3-lower alkyl-ureido or 3-cycloalkyl-ureido, in which cycloalkyl has, for example, 5–7 ring members, for example 3-methylureido, 3-ethylureido or 3-cyclohexylureido.

N-Lower alkylamino and N,N-di-lower alkylamino are, for example, methylamino, ethylamino, dimethylamino or diethylamino.

Lower alkyleneamino preferably contains 5–7 ring carbon atoms and is, for example, pyrrolidino or piperidino.

Lower oxaalkyleneamino is, in particular, morpholino, whilst lower azaalkyleneamino is, in particular, corresponding N-lower alkyl-lower azaalkyleneamino, for example 4-methyl-1-piperazino.

Substituted lower alkyl groups are, for example, hydroxy-lower alkyl, lower alkoxy-lower alkyl, halogeno-lower alkyl, lower alkanoylamino-lower alkyl or lower alkoxycarbonylamino-lower alkyl.

Hydroxy-lower alkyl is preferably hydroxymethyl or 1- and in particular 2-hydroxyethyl.

Lower alkoxy-lower alkyl is preferably lower alkoxymethyl or 1- and in particular 2-lower alkoxy-ethyl, for example methoxymethyl, ethoxymethyl, 2-methoxy-ethyl or 2-ethoxy-ethyl.

Halogeno-lower alkyl radicals are in particular those which are derived from the said alkyl radicals and in which the halogen atom is a bromine atom or especially a chlorine atom or fluorine atom, for example chloromethyl, 2-chloroethyl, dichloromethyl and especially trifluoromethyl.

Lower alkoxycarbonylamino-lower alkyl groups are understood as meaning, for example, those radicals in which the lower alkyl moieties are derived from the said lower alkyl groups. Such groups are, for example, methoxycarbonylaminomethyl, ethoxycarbonylaminomethyl, 4-methoxycarbonylamino-n-butyl, 2-ethoxycarbonylaminoethyl, 3-ethoxycarbonylamino-n-propyl and especially 2-methoxycarbonylamino-ethyl and 3-methoxycarbonylamino-n-propyl, carbamoylmethyl or 2-carbamoylethyl.

Lower alkanoylamino-lower alkyl is especially lower alkanoylaminomethyl or 1- and in particular 2-lower alkanoylamino-ethyl, for example acetylaminomethyl, 2-acetylamino-ethyl or 2-propionylamino-ethyl.

The novel compounds have valuable pharmacological properties. Thus, they have a long-lasting hypotensive action, as can be shown in animal experiments, for example on intravenous administration in doses of about 0.01–1.0 mg/kg to narcotised cats.

In addition, the novel compounds exhibit sympathicolytical effects. The noradrenolytic action, which can be shown in vitro, for example in experiments on isolated vas deferens from rats in concentrations of 0.001–0.1 $\mu$M. Furthermore, the novel compounds inhibit unspecific tachycardial activities, as can also be shown in animal experiments, for example in vitro experiments in concentrations of 0.3–1.0 $\mu$g/ml on isolated guinea pig hearts prepared by the Langendorff method (inhibition of tachycardia by isoproterenol [$5 \times 10^{-9}$ $\mu$g/ml] or histamine [$3 \times 10^{-7}$ $\mu$g/ml]). On isolated guinea pig atria, these compounds lower the spontaneous frequency and increase the contraction force and thus have a negative chromotropic action and at the same time a positive inotropic action, in concentrations of 0.1–10 $\mu$g/ml. Moreover, the new compounds extend the functional time of refraction on the isolated guinea pig artria.

The novel compounds can accordingly be used as antihypertensive agents or as agents for treating cardiac insufficiency or coronary heart disease. Furthermore, they can be used as starting materials or intermediates for the preparation of other compounds, especially compounds having a therapeutic action.

Preferred compounds are those of the formula Ia

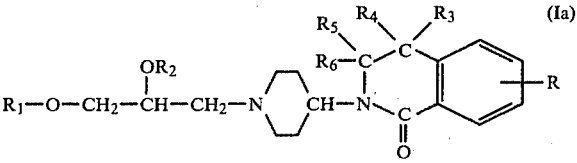

in which $R_1$ is substituted or unsubstituted monocyclic heteroaryl or benzoheteroaryl having 5 to 6 ring members and 1 or 2 ring nitrogen atoms, and substituents of the heterocyclic aryl radical can be substituted or unsubstituted lower alkyl, for example lower alkyl, lower alkoxy-lower alkyl, lower alkanoylamino-lower alkyl or lower alkoxycarbonylamino-lower alkyl, or free, etherified or esterified hydroxyl or mercapto, for example lower alkoxy, lower alkoxy-lower alkoxy, lower alkylthio-lower alkoxy, lower alkylthio or halogen, $R_2$ is a lower alkanoyl radical, such as, especially, the acetyl, propionyl or pivaloyl radical, or, in particular, a hydrogen atom, $R_3$ is a hydrogen atom or a hydroxyl group and $R_5$ is a hydrogen atom, or $R_3$ and $R_5$ together are a second bond and $R_4$ and $R_6$ are each a hydrogen atom, or $R_4$ together with $R_3$ is an oxo group and $R_5$ and $R_6$ are each a hydrogen atom, or $R_6$ together with $R_5$ is an oxo group and $R_3$ and $R_4$ are each a hydrogen atom, and R is a lower alkanoylamino radical, an amino group, a nitro group or, in particular, a lower alkyl radical, a lower alkoxy group, a halogen atom, a trifluoromethyl radical, a hydroxyl group or, in particular, a hydrogen atom, and salts thereof.

The invention relates especially to compounds of the formula Ia in which $R_1$ is monocyclic monoazaaryl or diazaaryl having six ring members, which is unsubstituted or substituted by lower alkyl, for example methyl, lower alkoxy, for example methoxy, lower alkylthio, for example methylthio or ethylthio, and/or halogen with an atomic number of not more than 35, for example chlorine or bromine, such as pyridyl, for example 2-, 3- or 4-pyridyl, pyrimidinyl, for example 2- or 4-pyrimidinyl, or pyrazinyl, for example 2-pyrazinyl, $R_2$ is lower alkanoyl, for example an acetyl, propionyl or, especially, pivaloyl radical, or in particular a hydrogen atom, $R_3$ is a hydrogen atom or a hydroxyl group and $R_5$ is a hydrogen atom, or $R_3$ and $R_5$ together are a second bond and $R_4$ and $R_6$ are each a hydrogen atom, or $R_4$ together with $R_3$ is an oxo group and $R_5$ and $R_6$ are each a hydrogen atom, or $R_6$ together with $R_5$ is an oxo group and $R_3$ and $R_4$ are each a hydrogen atom, and in particular $R_4$ and $R_6$ are each hydrogen and $R_3$ and $R_5$ either are a second bond or are each a hydrogen atom, and R is a lower alkyl radical, for example methyl, a lower alkoxy radical, for example methoxy, a halogen atom, for example chlorine, a trifluoromethyl radical or, in particular, a hydrogen atom, and salts thereof.

The invention relates especially to compounds of the formula Ia in which $R_1$ is 2-pyrazinyl which is unsubstituted or substituted by lower alkyl, for example by methyl, lower alkoxy, for example methoxy, lower alkylthio, for example methylthio or ethylthio, and/or halogen with an atomic number of not more than 35, for example chlorine or bromine, as well as unsubstituted or correspondingly substituted pyridyl, for example 2- or 3-pyridyl, substituents being able to assume any position, but at least one substituent preferably assuming the ortho-position relative to the linking ring carbon atom of the heteroaryl radical, and $R_2$, $R_3$, $R_4$, $R_5$, $R_6$ and R are as defined in the previous paragraph, or non-toxic acid addition salts thereof.

The invention relates in particular to compounds of the formula Ia in which $R_1$ is 2-pyrazinyl and also pyridyl, for example 2- or 3-pyridyl, which in the orthoposition relative to the linking carbon atom are preferably substituted by lower alkyl, for example methyl, lower alkoxy, for example methoxy, lower alkylthio, for example methylthio or ethylthio, or halogen with an atomic number of not more than 35, for example chlorine or bromine, and can contain further substituents of this type, and $R_2$, $R_3$, $R_4$, $R_5$, $R_6$ and R are hydrogen, and salts, especially acid addition salts and in particular pharmaceutically usable, non-toxic acid addition salts thereof. Preferred compounds are those described in the examples, especially those of the formula I which contain a preferably substituted 2-pyrazinyl radical as $R_1$ and in which $R_2$, $R_3$, $R_4$, $R_5$, $R_6$ and R are hydrogen, and the non-toxic acid addition salts thereof.

Further preferred compounds are those of the formula Ib

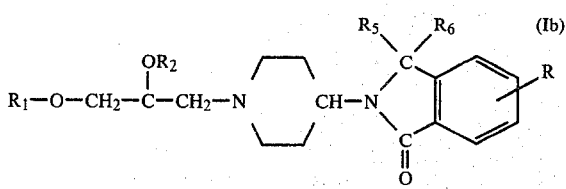

in which $R_1$ is substituted or unsubstituted monocyclic heteroaryl or benzoheteroaryl having 5 to 6 ring members and 1 or 2 ring nitrogen atoms, and substituents of the heterocyclic aryl radical can be substituted or unsubstituted lower alkyl, for example lower alkyl, lower alkoxy-lower alkyl, lower alkanoylamino-lower alkyl or lower alkoxycarbonylamino-lower alkyl, or free, etherified or esterified hydroxyl or mercapto, for example lower alkoxy, lower alkoxy-lower alkoxy, lower alkylthio-lower alkoxy, lower alkylthio or halogen, and R is a hydrogen atom, a lower alkyl radical, a hydroxyl group, a lower alkoxy radical, a halogen atom, a trifluoromethyl group, a nitro group, an amino group or a lower alkanoylamino group, $R_2$ is a hydrogen atom or a lower alkanoyl group, especially the acetyl, propionyl or pivaloyl radical, and $R_5$ and $R_6$ are each a hydrogen atom, or $R_5$ and $R_6$ together are an oxo group, and salts thereof. In the said compounds, the substituent R is preferably in the metaposition relative to the carbonyl group and in the paraposition relative to the methylene group.

The invention relates especially to compounds of the formula Ib in which $R_1$ is 2-pyrazinyl which is unsubstituted or substituted by lower alkyl, for example by methyl, lower alkoxy, for example methoxy, lower alkylthio, for example methyltho or ethylthio, and/or halogen with an atomic number of not more than 35, for example chlorine or bromine, and also unsubstituted or correspondingly substituted pyridyl, for example 2- or 3-pyridyl, substituents being able to assume any position, but at least one substituent preferably assuming the ortho-position relative to the linking ring carbon atom of the heteroaryl radical, R is a hydrogen atom or a methyl, methoxy or acetylamino group, $R_2$ is a hydrogen atom or a lower alkanoyl group, for example the acetyl, propionyl or pivaloyl group, and $R_5$ and $R_6$ are each a hydrogen atom, and salts thereof.

The invention relates in particular to compounds of the formula Ib in which $R_1$ is 2-pyrazinyl and also pyridyl, for example 2- or 3-pyridyl, which in the orthoposition relative to the linking carbon atom is preferably substituted by lower alkyl, for example methyl, lower alkoxy, for example methoxy, lower alkylthio, for example methylthio or ethylthio, or halogen with an atomic number of not more than 35, for example chlorine or bromine, and can contain further substituents of this type, and $R_2$ is a hydrogen atom or an acetyl, propionyl or pivaloyl group and R, $R_5$ and $R_6$ are each a hydrogen atom, and the non-toxic acid addition salts thereof.

The invention relates especially to compounds of the formula Ib in which $R_1$ is monocyclic monoazaaryl or diazaaryl having six ring members, which is unsubstituted or substituted by lower alkyl, for example methyl, lower alkoxy, or example methoxy, lower alkylthio, for example methylthio or ethylthio, and/or halogen with an atomic number of not more than 35, for example chlorine or bromine, such as pyridyl, for example 2-, 3- or 4-pyridyl, pyrimidinyl, for example 2- or 4-pyrimidinyl, or pyrazinyl, for example 2-pyrazinyl, and R, $R_2$, $R_5$ and $R_6$ are each a hydrogen atom, and the non-toxic acid addition salts thereof.

The novel compounds of the formula I are obtained by methods known per se.

For example, a compound of the formula

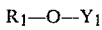 (II)

can be reacted with a compound of the formula

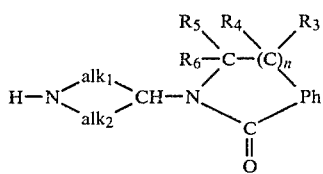 (III)

in which formulae $R_1$, $alk_1$, $alk_2$, Ph, n, $R_3$, $R_4$, $R_5$ and $R_6$ are as defined, $Y_1$ is a radical of the formula

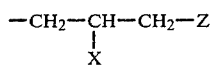

and X is the group $R_2$, where $R_2$ is as defined, and Z is a reactive esterified hydroxyl group, or X and Z together form an epoxy group.

Furthermore, a compound of the formula

 (IIa)

in which $R_1$ is as defined above, can be reacted with a compound of the formula

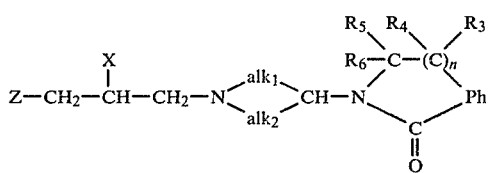 (IIIa)

in which X, Z, $alk_1$, $alk_2$, Ph, n, $R_3$, $R_4$, $R_5$ and $R_6$ are as defined above.

This reaction is carried out in the customary manner. If the starting material used is a reactive ester, the compound of the formula IIa is preferably used in the form of its metal phenolate, such as an alkali metal phenolate, for example the sodium phenolate, or the reaction is carried out in the presence of an acid-binding agent, especially of a condensing agent, which can form a salt with the compound of the formula IIa, such as an alkali metal alcoholate.

Furthermore, the novel compounds in which $R_3$ is hydroxyl can be prepared by reducing the oxo group in the propyl chain of a compound of the formula

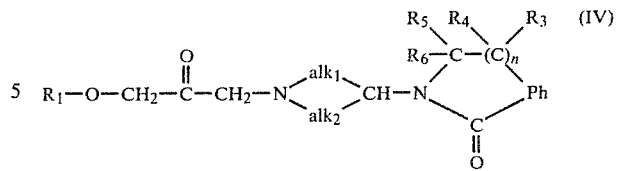 (IV)

in which $R_1$, $alk_1$, $alk_2$, Ph, n, $R_3$, $R_4$, $R_5$ and $R_6$ are as defined above, to a hydroxyl group.

This reduction is carried out in a conventional manner, especially using a di-(light metal) hydride, such as sodium borohydride. However, the reduction can also be carried out with nascent hydrogen. Nascent hydrogen can be obtained by the action of metal or metal alloys on hydrogen donors, such as a carboxylic acid, alcohols or water, the substances used being in particular zinc or zinc alloys together with acetic acid, or an alkali metal and an alcohol, such as sodium and ethanol.

Furthermore, the reduction can be carried out by catalytic hydrogenation, such as with hydrogen in the presence of a hydrogenation catalyst, for example heavy metals, such as palladium, platinum or Raney nickel. Care must be taken that other reducible groups are not attacked during the reduction.

Furthermore, the novel compounds can be obtained by reducing the pyridinium ring in a compound of the formula

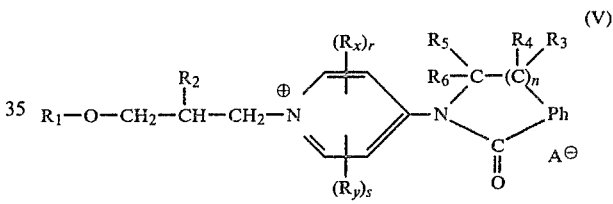 (V)

in which $R_1$, $R_2$, $R_3$, $R_4$, $R_5$, $R_6$, Ph and n are as defined above, $R_x$ and $R_y$ independently of one another are lower alkyl radicals or hydrogen atoms and r and s are 1 or 2 and $A^\ominus$ is an anion, to the paperidine ring.

The reduction can be carried out in a conventional manner, preferably by catalytic hydrogenation, such as with hydrogen in the presence of a hydrogenation catalyst, for example heavy metals, such as palladium, platinum or Raney nickel, or with nascent hydrogen, such as, for example, sodium and an alcohol, such as a lower alkanol, for example ethanol. Care must be taken that other reducible groups are not attacked during the reduction.

Furthermore, the novel compounds can be obtained by subjecting a compound of the formula

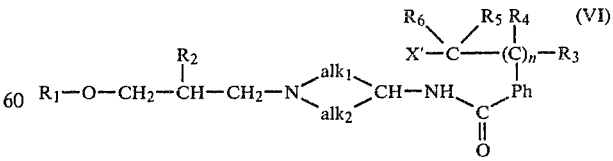 (VI)

in which $R_1$, $R_2$, $alk_1$, $alk_2$, Ph, n, $R_3$, $R_4$, $R_5$ and $R_6$ are as defined and X' is a reactive esterified hydroxyl group, to an intramolecular condensation reaction.

A reactive esterified hydroxyl group is especially one of those mentioned above.

The cyclisation (intramolecular condensation) can be carried out in a conventional manner, preferably in the presence of a solvent, such as of an inert polar solvent, such as an alcohol, for example ethanol or isopropanol, or dimethylformamide, and advantageously in the presence of a condensing agent, especially of a basic condensing agent. Preferably, the reaction is carried out in the presence of an alkali metal hydroxide, carbonate or bicarbonate or alkaline earth metal hydroxide, carbonate or bicarbonate, for example sodium hydroxide, potassium hydroxide, calcium hydroxide, sodium carbonate, potassium carbonate, calcium carbonate, sodium bicarbonate or potassium bicarbonate, or of an alkali metal acetate, such as sodium acetate, or of an alkali metal alcoholate, such as sodium methylate, or organic tertiary nitrogen bases, such as trialkylamines, for example trimethylamine or triethylamine, or pyridine.

The novel compounds in which $R_3$ and $R_5$ together are a second bond, when n is 1, can also be obtained by reacting a compound of the formula

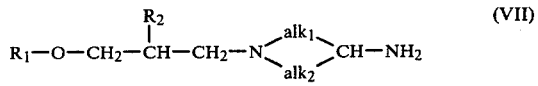

with a compound of the formula

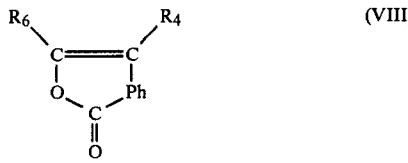

in which formulae $R_1$, $R_2$, $R_4$, $R_6$, $alk_1$, $alk_2$ and Ph are as defined.

The reaction can be carried out in a manner known per se. Advantageously, the reaction is carried out in the presence of an organic base, such as a tertiary amine, in particular pyridine, and this base can at the same time also serve as the solvent. However, the reaction can also be carried out in the presence of further solvents.

Furthermore, the novel compounds can be obtained by subjecting a compound of the formula

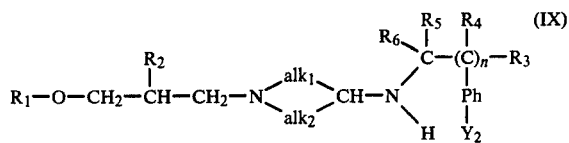

in which $R_1$, $R_2$, $alk_1$, $alk_2$, $R_3$, $R_4$, $R_5$, $R_6$, n and Ph are as defined and $Y_2$ is a free carboxyl group or preferably a functionally modified carboxyl group containing an oxo group, to an intramolecular condensation reaction.

A functionally modified carboxyl group containing an oxo group is, for example, an esterified carboxyl group, such as, in particular, a carboxyl group esterified with a lower alkanol or aralkanol, such as methanol, phenol, p-nitrophenol or benzyl alcohol, or an activated esterified carboxyl group, such as a carboxyl group esterified with cyanomethanol, or an acid halide grouping, such as, in particular, an acid chloride grouping, or an acid azide, acid amide or acid anhydride grouping. Acid anhydride groupings are in particular those of mixed anhydrides, especially of mixed anhydrides with carbonic acid monoalkyl esters, such as carbonic acid monoethyl or monoisobutyl ester.

The reaction can be carried out in a conventional manner. Preferably, the reaction is carried out at elevated temperature. The reaction is advantageously carried out in a solvent, such as an inert solvent, for example a hydrocarbon, such as benzene or toluene, or in a high-boiling inert solvent, for example diphenyl ether.

Furthermore, the novel compounds in which $R_2$ is hydrogen can be obtained by detaching $R_2$, by hydrogenolysis, from a compound of the formula

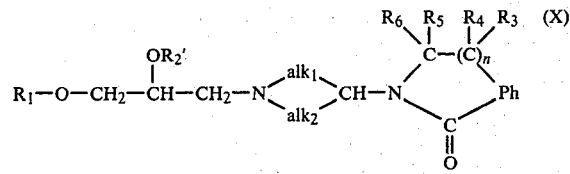

in which $R_1$, $alk_1$, $alk_2$, Ph, n, $R_3$, $R_4$, $R_5$ and $R_6$ are as defined and $R_2$ is a radical detachable by hydrogenolysis.

A radical detachable by hydrogenolysis is, in particular, an α-aralkyl radical, such as the benzyl radical, or an α-aralkoxycarbonyl radical, such as the carbobenzoxy radical. The hydrogenolysis can be carried out in a conventional manner, preferably by means of hydrogen in the presence of a hydrogenation catalyst, such as a nickel, palladium, platinum or ruthenium catalyst.

Furthermore, the novel compounds of the formula I in which $R_6$ together with $R_5$ forms an oxo group can be obtained by reacting a compound of the formula

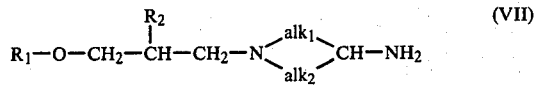

in which $R_1$, $R_2$, $alk_1$ and $alk_2$ are as defined above, with a compound of the formula

in which $R_3$, $R_4$, n and Ph are as defined above and the substituents $Y_3$ independently of one another are a free carboxyl group or preferably a functionally modified carboxyl group containing an oxo group, or together are the grouping

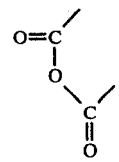

A functionally modified carboxyl group containing an oxo group is, for example, an esterified carboxyl group, such as, in particular, a carboxyl group esterified with a lower alkanol or aralkanol, such as methanol, phenol, p-nitrophenol or benzyl alcohol, or an activated esterified carboxyl group, such as a carboxyl group esterified with cyanomethanol, or an acid halide grouping, such as, in particular, an acid chloride grouping, or an acid azide, acid amide or acid anhydride grouping. Acid anhydride groupings are, in particular, those of mixed anhydrides, especially of mixed anhydrides with carbonic acid monoalkyl esters, such as carbonic acid monoethyl or monoisobutyl ester.

The reaction can be carried out in a conventional manner. Preferably, the reaction is carried out at elevated temperature. The reaction is advantageously carried out in a solvent, such as an inert solvent, for example a hydrocarbon, such as benzene or toluene, or in a high-boiling inert solvent, for example diphenyl ether.

In resulting compounds, substituents can be detached, introduced or converted, within the scope of the end products.

Thus, in compounds of the formula I containing unsaturated substituents, for example lower alkenyl, lower alkenyloxy or lower alkynyloxy, these can be reduced by suitable reduction methods to give corresponding saturated compounds or, in the case of substituents containing a triple bond, to give compounds containing a double bond. The reducing agent used is preferably catalytically activated hydrogen and, in the case of a triple bond, also a chemical reducing agent, such as sodium in the presence of liquid ammonia.

In a resulting compound of the formula I which contains halogen, such as bromine or iodine, as a substituent of an aromatic radical, this halogen can also be replaced by trifluoromethyl, for example by treatment with trifluoromethyl iodide in the presence of copper powder and of a suitable aprotic solvent, such as pyridine, dimethylformamide or acetonitrile.

In a resulting compound of the formula I, an α-phenyl-lower alkyl group, for example, in benzyloxy, can be detached by treating the corresponding compound with catalytically activated hydrogen and replaced by hydrogen, for example a benzyloxy group can be replaced by hydroxyl.

Furthermore, in a compound of the formula I, which contains hydroxyl or mercapto, in the form of a primary carbinol group or of a phenolic hydroxyl group, as a substituent, this, which can be in the form of a salt, for example in the form of an alkali metal salt, can be converted to etherified hydroxyl or mercapto, for example lower alkoxy or lower alkylthio, by treatment with a reactive ester of an alcohol, such as a substituted or unsubstituted lower alkyl halide. Moreover, it is possible to react hydroxyl in a hydroxy-lower alkyl or hydroxy-lower alkoxy substituent, usually in the form of a reactive esterified hydroxyl group, such as halogen, for example chlorine, with an alcohol, for example a lower alkanol, or a mercaptan, for example a lower alkylmercaptan, preferably in the presence of a basic agent which is able, for example, to convert an alcohol or a mercaptan into a metal compound, and thus to obtain compounds of the formula I which contain correspondingly etherified hydroxy- or mercapto-lower alkyl or -lower alkoxy. Furthermore, in a resulting compound, a reactive esterified hydroxyl group, such as halogen, for example chlorine, especially in the α-position relative to a ring nitrogen atom in a radical $R_1$, can be converted to an etherified or esterified hydroxyl or mercapto group, for example to lower alkoxy or lower alkylthio, for example by treatment with an alcoholate or thio-alcoholate compound, such as an alkali metal lower alkanolate or thio-lower alkanolate, for example a sodium lower alkanolate or thio-lower alkanolate or potassium lower alkanolate or thio-lower alkanolate.

In a compound of the formula I, a propargyloxy group can be converted to the acetonyloxy group, for example by hydration in an acid medium and in the presence of a mercury-II salt, for example by treatment with an aqueous mineral acid, for example dilute hydrochloric or sulphuric acid, in the presence of mercury-II chloride.

In a compound of the formula I which contains primary amino as a substituent, the latter can also be substituted; thus, amino can be acylated, for example by treating the amino compound with a suitable acid derivative, such as an anhydride, which can be a mixed anhydride, for example a corresponding chloride, if necessary in the presence of a basic agent.

Furthermore, in compounds of the formula I in which Ph is an o-phenylene radical containing an amino group, the said amino group can be acylated, for example by reaction with an acylating agent.

Acylating agents are carboxylic acids, for example aliphatic, araliphatic or cycloaliphatic carboxylic acids, preferably in the form of their functional derivatives, such as halides, especially chlorides, or anhydrides, for example pure or mixed anhydrides, or inner anhydrides, such as ketenes.

Furthermore, in compounds of the formula I which contain hydroxyl groups, these can be acylated (esterified). The acylation is carried out in a conventional manner, for example by reaction with carboxylic acids, advantageously in the form of their reactive functional derivatives, such as acid halides, for example chlorides, esters, especially esters with lower alkanols, such as methanol and ethanol, or activated esters, such as the cyanomethyl esters, or pure or mixed anhydrides, for example mixed anhydrides with carbonic acid monoalkyl esters, such as carbonic acid monoethyl and monoisobutyl esters.

In compounds of the formula I which contain an acylated hydroxyl or amino group, this can be split in a conventional manner to give the free hydroxyl or amino group, especially by hydrolysis, the reaction being catalysed, as appropriate, by acid or basic compounds, for example by inorganic acids or alkali metal hydroxide solutions (bases), for example by hydrochloric acid or by sodium hydroxide solution. If splitting of this type should already occur in the course of one of the above methods of preparation, a resulting free hydroxyl or amino group can, if desired, be acylated as described above.

Furthermore, in compounds of the formula I which contain substituents with a C-C double or triple bond, the C-C double or triple bond can be converted to a C-C single bond by catalytic hydrogenation, such as by hydrogen in the presence of a hydrogenation catalyst, for example nickel, platinum or palladium, such as Raney nickel, platinum black or palladium-on-active charcoal. Care must be taken that other reducible groups are not attacked.

In compounds of the formula I which contain substituents with a C-C triple bond, it is also possible to reduce this only to a C-C double bond and, if desired, stereospecifically to a C-C cis- or C-C trans-double bond. The reduction of a C-C triple bond to a C-C double bond can be effected, for example, by hydrogenation with 1 mol of hydrogen in the presence of a less active hydrogenation catalyst, such as iron or palladium, for example Raney iron or palladium-on-barium sulphate, especially at elevated temperature. The reduction to a C-C cis-double bond can be effected, for example, by means of 1 mol of hydrogen in the presence of a deactivated catalyst, such as palladium-on-animal charcoal in the presence of quinoline, palladium-on-calcium carbonate in the presence of lead salts, or Raney nickel. The reduction to a C-C trans-double bond can be effected, for example, by means of sodium in liquid ammonia, and in this case, especially taken a urea group into consideration, short reaction times and no excess of reducing agent are used, and, if desired, an ammonium halide, such as ammonium chloride, is added as a catalyst.

In resulting compounds of the formula I which have nitro groups on an aromatic nucleus, these groups can be reduced to amino groups.

The reduction can be carried out in a conventional manner, for example by means of nascent hydrogen (for example with iron and hydrochloric acid or with aluminum amalgam) or with catalytically activated hydrogen, such as hydrogen in the presence of platinum, nickel or palladium catalysts.

Furthermore, compounds of the formula I in which $R_3$ and $R_4$ together are an oxo group can be reduced to compounds in which $R_3$ is hydroxyl and $R_4$ is hydrogen.

The reduction of the oxo group is effected in a conventional manner, for example by metallic reduction, such as by treatment with sodium in alcohol, or with complex metal hydrides, such as sodium borohydride, or by catalytically activated hydrogen, for example hydrogen in the presence of a platinum, palladium, nickel or copper catalyst, such as platinum oxide, palladium-on-charcoal, Raney nickel or copper chromite. The reaction is preferably carried out in the presence of diluents and/or solvents, at low, normal or elevated temperature, in an open vessel or in a closed vessel under pressure.

The reduction of the oxo group can also be effected by the Meerwein-Ponndorf-Verley method. Thus, for example, the oxo compound can be treated in a conventional manner with a lower alkanol, such as isopropanol, in the presence of a corresponding alkanolate, such as aluminum isopropylate.

Furthermore, in compounds of the formula I in which $R_3$ is hydroxyl, the hydroxyl group can be detached. This yields compounds in which $R_3$ and $R_5$ are a second bond.

Detaching can be effected in a conventional manner, for example by treatment with strong acids, such as sulphuric acid, p-toluenesulphonic acid, concentrated hydrochloric acid, oxalic acid or other dehydrating agents, such as phosphorus pentoxide, zinc chloride or boron trioxide. If desired, the water is removed by means of a water separator. For example, the reaction can be carried out in a boiling hydrocarbon, such as benzene or toluene.

Furthermore, in compounds of the formula I in which $R_3$ is hydroxyl, the hydroxyl group can be replaced by hydrogen. This can be effected, for example, by catalytic hydrogenation.

Furthermore, compounds of the formula I in which $R_3$ and $R_5$ are a second bond can be hydrogenated to compounds in which $R_3$ and $R_5$ are hydrogen atoms. This can be effected in particular by catalytic hydrogenation.

The catalytic hydrogenation can be carried out in a conventional manner, especially by means of hydrogen in the presence of a hydrogenation catalyst, such as a palladium, platinum or nickel catalyst.

The said reactions can, as desired, be carried out at the same time or successively and in any order.

The said reactions can be carried out in a conventional manner, in the presence or absence of solvents or diluents, acid or basic condensing agents and/or catalysts, at lowered, normal or elevated temperature, if necessary in a closed vessel under elevated pressure and/or under an inert gas atmosphere.

Depending on the process conditions and starting materials, the end products are obtained in the free form or in the form of their acid addition salts, which salts also constitute a subject of the invention. Thus, for example, basic, neutral or mixed salts, and in some cases also hemi-, mono-, sesqui- or poly-hydrates thereof, can be obtained. The acid addition salts of the novel compounds can be converted into the free compound in a manner known per se, for example using basic agents, such as alkalis or ion exchangers. On the other hand, the resulting free bases can form salts with organic or inorganic acids. The acids used to prepare acid addition salts are in particular those which are suitable for forming therapeutically usable salts. Examples of such acids are: hydrogen halide acids, for example hydrochloric acid, sulphuric acids, for example sulphuric acid, phosphoric acids, nitric acid, perchloric acid, aliphatic, alicyclic, aromatic or heterocyclic carboxylic or sulphonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid, fumaric acid, benzoic acid, p-aminobenzoic acid, anthranilic acid, p-hydroxybenzoic acid, salicylic acid or p-aminosalicylic acid, embonic acid, methanesulphonic acid, ethanesulphonic acid, hydroxyethanesulphonic acid, ethylenesulphonic acid, a halogenobenzenesulphonic acid, toluenesulphonic acid, naphthalenesulphonic acid or sulphanilic acid; methionine, tryptophan, lysine or arginine.

These and other salts of the novel compounds, for example the picrates, can also be used to purify the resulting free bases, by converting the free bases into salts, separating these off and again liberating the bases from the salts. Because of the close relationship between the novel compounds in the free form and in the form of their salts, what is stated in this specification in respect of the free compounds also applies by analogy to the corresponding salts.

The invention also relates to those embodiments of the process in which a compound obtainable as an intermediate at any stage of the process is used as the starting material and the missing process steps are carried out, or the process is discontinued at any stage, or in which a starting material is formed under the reaction conditions, or in which a reactant can be in the form of an optical antipode and/or of a salt.

Thus, for example, the novel piperidines can be obtained by reacting a compound of the formula

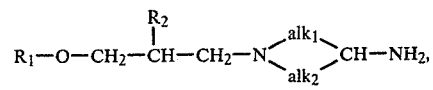

in which $R_1$, $R_2$, $alk_1$ and $alk_2$ are as defined, with a compound of the formula

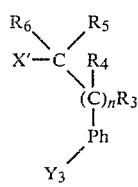

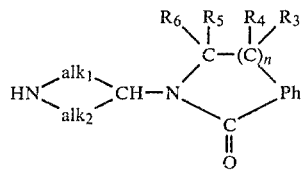

in which n, $R_3$, $R_4$, $R_5$ and $R_6$ are as defined and $X'$ and $Y_3$ are as defined under formula VI and IX respectively. A compound of the formula VI is formed as an intermediate and this then further reacts according to the invention to give the compound of the formula I. The reaction can be carried out in a conventional manner, for example as described above for the intramolecular condensation reactions.

Depending on the choice of the starting materials and procedures, the novel compounds can be in the form of optical antipodes or racemates or, if they contain at least 2 asymmetric carbon atoms, also in the form of mixtures of racemates and/or of pure geometric isomers or in the form of mixtures thereof (mixtures of isomers).

Resulting mixtures of isomers can be separated into the two pure geometric isomers in a known manner on the basis of the physico-chemical differences between the constituents, for example by chromatography on a suitable stationary phase, such as with a complex-forming heavy metal compound, for example with a silver compound, pretreated silica gel or aluminium oxide, or by forming a heavy metal adduct, for example the silver nitrate complex, separating the latter into the adducts of the pure isomers, for example by fractional crystallisation, and subsequently setting free the pure isomers.

Resulting pure isomers, for example trans-isomers, can be converted into the isomers of opposite configuration, for example into the cis-isomers, in a conventional manner, for example photochemically, for example by irradiation with light of suitable wavelength, advantageously in a suitable solvent, such as an aliphatic hydrocarbon, or in the presence of a suitable catalyst.

Mixtures of racemates can be separated into the two stereoisomeric (diasteromeric) pure racemates in a known manner on the basis of the physico-chemical differences between the constituents, for example by chromatography and/or fractional crystallisation.

Resulting racemates can be resolved by known methods, for example by recrystallisation from an optically active solvent, with the aid of microorganisms or by reaction with an optically active acid which forms salts with the racemic compound and separation of the salts obtained in this way, for example on the basis of their different solubilities, into the diastereomers, from which the antipodes can be set free by the action of suitable agents. Optically active acids particularly commonly used are, for example, the D- and L-forms of tartaric acid, di-o-toluyltartaric acid, malic acid, mandelic acid, camphorsulphonic acid or quinic acid. Advantageously, the more active L-antipode is isolated.

The starting materials used for carrying out the reactions according to the invention are preferably those which result in the groups of end products mentioned in particular initially and especially in the end products specifically described or singled out.

The starting materials are known or, if they are novel, can be obtained by methods known per se.

The compounds of the formula which are used as preferred starting materials, can be obtained, for example, by reacting a compound of the formula

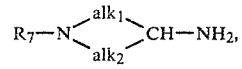

in which $alk_1$ and $alk_2$ are as defined and $R_7$ is an α-aralkyl radical, such as a benzyl radical, with a compound of the formula

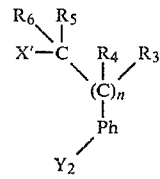

in which n, $R_3$, $R_4$, $R_5$ and $R_6$ are as defined and $X'$ and $Y_2$ are as defined under formulae VI and IX respectively, and, in the resulting compound of the formula

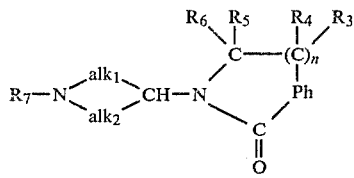

replacing the α-aralkyl radical $R_7$ by hydrogen, for example by catalytic hydrogenation as described above.

The novel compounds can be used as medicines, for example in the form of pharmaceutical preparations, which contain them or their salts in a mixture with a pharmaceutical, organic or inorganic, solid or liquid carrier which is suitable, for example, for enteral, for example, oral, or parenteral administration. Carriers are those substances which do not react with the novel compounds, for example water, gelatin, lactose, starch, magnesium stearate, talc, vegetable oils, benzyl alcohols, gum, polyalkylene glycols, white petroleum jelly, cholesterol or other known medicinal carriers. The pharmaceutical preparations can be, for example, in the form of tablets, sugar-coated tablets, capsules, suppositories, ointments or creams or in liquid form as solutions (for example as an elixir or syrup), suspensions or emulsions. They can be sterilised and/or contain adjuncts, such as preservatives, stabilisers, wetting agents or emulsifiers, salts for changing the osmotic pressure or buffers. They can also contain yet further therapeutically valuable substances. The preparations, which can also be used in veterinary medicine, are obtained by conventional methods.

The dosage of the novel compounds depends on the nature of the conditions to be treated and on the individual needs. For example, the novel compounds can be administered to a warm-blooded animal with a body weight of about 75 kg in a daily dose of about 5–100 mg and especially of about 5 to 60 mg.

The novel compounds can also advantageously be used in pharmaceutical preparations in combination with other antihypertensive agents and/or diuretics.

Compounds having an antihypertensive action are, in particular, those of the α-amino-β-hydroxyphenylpropionic acid and β-amino-β-alkoxyphenyl-propionic acid type and especially of the hydrazinopyridazine type and of the sympathicolytic agent type.

Suitable diuretics are substances which increase diuresis both by renal and by extrarenal action on the tissues. Such substances are substances which have an inhibitory action on the back-resorption in the tubulus, for example, in particular, saluretics and also ethacrynic acid and analogues thereof.

Particularly suitable substances are benzothiadiazine derivatives, such as thiazides and hydrothiazides, benzenesulphonamides, phenoxyacetic acids, benzofuran-2-carboxylic acids and benzofuran-2,3-dihydro-2-carboxylic acids.

The following examples illustrate the invention without restricting it. The temperatures are in degrees centigrade.

EXAMPLE 1

24.2 g (0.13 mol) of 2-chloro-3-(2,3-epoxypropoxy)-pyrazine and 23 g (0.1 mol) of 1-(4-piperiyl)-3,4-dihydro-1(2H)-isoquinolone in 250 ml of isopropanol are stirred for 24 hours at about 20°. The crystals which have precipitated out are filtered off with suction and washed with ether and yield 36.6 g of 2-{1-[3-(3-chloro-2-pyrazinyloxy)-2-hydroxy-1-propyl]-4-piperidyl}-3,4-dihydro-1(2H)-isoquinolone with a melting point of 115°–116°.

The hydrochloride prepared with alcoholic hydrochloric acid crystallises from alcohol; melting point 215° (decomposition).

EXAMPLE 2

13.5 g (0.032 mol) of 2-{1-[3-(3-chloro-2-pyrazinyloxy)-2-hydroxy-1-propyl]-4-piperidyl}-3,4-dihydro-1(2H)-isoquinolone and 1.95 g (0.036 mol) of sodium methylate in 150 ml of methanol are refluxed for 10 hours, with stirring. The reaction mixture is evaporated under a waterpump vacuum. The residue is dissolved in ethyl acetate and extracted with 2 N hydrochloric acid. The combined hydrochloric acid extracts are rendered alkaline with concentrated sodium hydroxide solution and extracted with methylene chloride. The combined methylene chloride extracts are washed with water, dried over sodium sulphate and evaporated under a waterpump vacuum. The residue crystallises from methanol/ether.

This yields 8.2 g of 2-{1-[3-(3-methoxy-2-pyrazinyloxy)-2-hydroxy-1-propyl]-4-piperidyl}-3,4-dihydro-1(2H)-isoquinolone with a melting point of 122°–124°.

The hydrochloride prepared with methanolic hydrochloric facid crystallises from water/acetone; melting point 167°–169°/190°–193°.

EXAMPLE 3

12.5 g (0.03 mol) of 2-{1-[3-(3-chloro-2-pyrazinyloxy)-2-hydroxy-1-propyl]-4-piperidyl}-3,4-dihydro-1(2H)isoquinolone, 2.78 g (0.045 mol) of ethyl mercaptan and 2.43 g (0.045 mol) of sodium methylate in 200 ml of methanol are refluxed for 10 hours, with stirring. The reaction mixture is totally evaporated under a waterpump vacuum. The residue is dissolved in methylene chloride and the solution is washed with water. The methylene chloride solution is extracted with 2 N hydrochloric acid. The combined hydrochloric acid extracts are rendered alkaline with concentrated sodium hydroxide solution and extracted with methylene chloride. The combined methylene chloride extracts are washed with water, dried over sodium sulphate and evaporated under a waterpump vacuum, whereupon the residue crystallises.

This yields 13 g of 2-{1-[3-(2-ethylthio-3-pyrazinyloxy)-2-hydroxy-1-propyl]-4-piperidyl}-3,4-dihydro-1(2H)-isoquinolone with a melting point of 136°–138°.

The hydrochloride prepared with methanolic hydrochloric acid crystallises from methanol/ether; melting point 200°–202°.

EXAMPLE 4

5 g of 1-[3-(3-methoxy-2-pyrazinyloxy)-2-hydroxy-1-propyl]-4-(3,4-dihydro-1(2H)-2-isoquinolonyl)-piperidinium bromide are hydrogenated with 2 g of $PtO_2$ in a mixture of 30 ml of water and 30 ml of ethanol at 40°. The catalyst is then filtered off and the filtrate is concentrated in vacuo. 2 N sodium hydroxide solution is added to the residue and the alkaline phase is extracted with ethyl acetate. The extract is dried, concentrated, and recrystallised from methanol/ether. The resulting 2-{1-[3-(3-methoxy-2-pyrazinyloxy)-2-hydroxy-1-propyl]-4-piperidyl}-3,4-dihydro-1(2H)-isoquinolone has a melting point of 122°–124°. The quaternary starting material is prepared by heating 3-(3-methoxy-2-pyrazinyloxy)-2-hydroxy-1-bromopropane with 2-(4-piperidinyl)-3,4-dihydro-1(2H)-isoquinolone at 100° in dimethyl formamide.

EXAMPLE 5

44.9 g of 1-[3-(3-methoxy-2-pyrazinyloxy)-2-hydroxy-1-propyl]-4-[2-(2-chloroethyl)-benzoylamino]-piperidine are dissolved in 200 ml of dimethyl formamide. Then 90 ml of 30% sodium methylate solution are slowly added dropwise to this solution and the reaction mixture is heated for 3 hours to 50°. The dimethyl formamide is then evaporated off in vacuo and the residue is dissolved in ethyl acetate and the organic phase is extracted with 2 N hydrochloric acid. The combined hydrochloric acid extracts are made alkaline with conc. sodium hydroxide solution and extracted with methylene chloride. The combined methylene chloride extracts are washed with water, dried over sodium sulphate and concentrated in vacuo. The residue is recrystallised from methanol/ether. The resulting 2-1-[3-(3-methoxy-2-pyrazinyloxy)-2-hydroxy-1-propyl]-4-piperidyl-3,4-dihydro-1(2H)-isoquinolone has a melting point of 122°–124°. The starting material is obtained by acylation of 1-[3-(3-methoxy-2-pyrazinyloxy)-2-hydroxy-1-propyl]-4-aminopiperidine with 2-(2-chloroethyl)-benzoyl chloride in acetone with the addition of triethylamine.

What is claimed is:

1. A compound corresponding to formula Ia

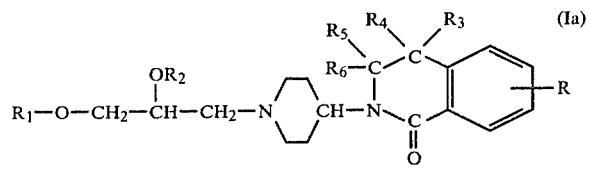 (Ia)

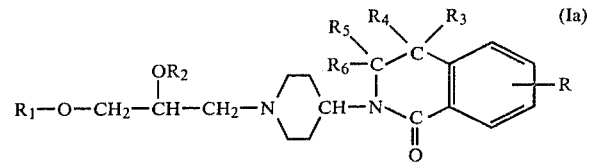 (Ia)

in which $R_1$ is pyrazinyl or pyrazinyl substituted by lower alkyl, lower alkoxy, lower alkylthio, and/or halogen with an atomic number of not more than 35, pyridyl or pyridyl substituted by lower alkyl lower alkoxy, lower alkylthio and/or halogen and an atomic number of not more than 35 $R_2$ is hydrogen or lower alkanoyl, $R_3$ is a hydrogen atom or a hydroxyl group and $R_5$ is hydrogen, or $R_3$ and $R_5$ together are a second bond and $R_4$ and $R_6$ are each a hydrogen atom, or $R_4$ together with $R_3$ is an oxo group and $R_5$ and $R_6$ are each a hydrogen atom, or $R_6$ together with $R_5$ is an oxo group and $R_3$ and $R_4$ are each a hydrogen atom, or $R_4$ and $R_6$ are each hydrogen and $R_3$ and $R_5$ either a second bond or are each a hydrogen atom, and R is hydrogen lower alkyl lower alkoxy halogen, or trifluoromethyl or a salt thereof.

2. A compound corresponding to formula Ia in which $R_1$ is 2-pyrazinyl or 2-pyrazinyl substituted by lower alkyl, lower alkoxy, lower alkylthio, or halogen with an atomic number of not more than 35, pyridyl or pyridyl substituted by lower alkyl lower alkoxy, lower alkylthio or halogen with an atomic number of not more than 35, and $R_2$, $R_3$, $R_4$, $R_5$, $R_6$ and R are hydrogen or a non-toxic acid addition salt thereof.

3. A compound as claimed in claim 1 and being the 2-[1-[3-(3-chloro-2-pyrazinyloxy)-2-hydroxy-1-propyl]-4-piperidyl]-3,4-dihydro-1(2H)-isoquinolone and a therapeutically useful acid addition salt thereof.

4. A compound as claimed in claim 1 and being the 2-[1-[3-(3-methoxy-2-pyrazinyloxy)-2-hydroxy-1-propyl]-4-piperidyl]-3,4-dihydro-1(2H)-isoquinolone and a therapeutically useful acid addition salt thereof.

5. A compound as claimed in claim 1 and being the 2-[1-[3-(3-ethylthio-2-pyrazinyloxy)-2-hydroxy-1-propyl]-4-piperidyl]-3,4-dihydro-1(2H)-isoquinolone and a therapeutically useful acid addition salt thereof.

* * * * *